United States Patent [19]  
Ecker

[11] 4,070,462  
[45] Jan. 24, 1978

[54] STEROID OINTMENT  
[75] Inventor: Varda Ecker, New York, N.Y.  
[73] Assignee: Schering Corporation, Kenilworth, N.J.  
[21] Appl. No.: 735,854  
[22] Filed: Oct. 26, 1976  
[51] Int. Cl.$^2$ .......................................... A61K 31/56  
[52] U.S. Cl. .................................................. 424/243  
[58] Field of Search ........................ 424/243; 260/397.45  
[56] References Cited  
U.S. PATENT DOCUMENTS

| | | | |
|---|---|---|---|
| 3,312,590 | 4/1967 | Elks et al. | 260/397.45 |
| 3,755,566 | 8/1973 | Irmascher et al. | 424/243 |
| 3,780,177 | 12/1973 | Ercoli et al. | 424/243 |
| 3,892,856 | 7/1975 | Hill et al. | 260/239.55 D |

Primary Examiner—Elbert L. Roberts  
Attorney, Agent, or Firm—Barbara L. Cowley Renda; Stephen B. Coan; Bruce M. Eisen

[57] ABSTRACT

An improved ointment for the topical administration of steroids is comprised of a therapeutically effective amount of a 17-mono or 17,21-diester of betamethasone in a non-aqueous base comprised of 5–15% of a glycol solvent, 1–3% of a principle emulsifying agent; 0–7% of a secondary emulsifying agent; and 70–90% of a petrolatum base.

18 Claims, No Drawings

STEROID OINTMENT

This invention relates to a topical ointment for use in the application of steroid medicaments and to mixtures of the ointment base and such steroids. More particularly, this invention relates to a new, improved ointment vehicle for steroids having advantages over previously known ointments.

The use of topical ointments as vehicles for steroid medicaments, particularly steroids having anti-inflammatory activity, is well-known in the art. The problem which must be dealt with in order to prepare a successful composition is to balance the completeness of incorporation of the steroidal medicament in the vehicle with the ease and completeness of its release from the ointment to and through the skin to which it is applied.

Topical steroids dispersed or incorporated in oil-in-water or water-in-oil emulsion-based vehicles have been observed to remain unabsorbed by the skin because the steroid is insoluble in such systems. Alternatively, a water-soluble steroid may be used which does dissolve in the aqueous phase of either the oil-in-water or the water-in-oil emulsion base, but when the steroid is exposed to the dermal surface, it is too vehicle-soluble for optimal absorption.

Preferred bases for ointments are oleaginous bases which form an occlusive covering on the skin, thereby inducing skin hydration through sweat accumulation at the skin-ointment interface. Hydration is advantageous in that it restores suppleness to dry skin. However, the incorporation of topical steroids in such bases suffers from the same lack of absorption as with the emulsion type of ointment base. Ointment bases of this kind are also decreasing in favor because they are greasy and difficult to remove from the skin and clothing due to their lack of water-washability.

An optimum manner of effecting solubilization of topical steroids while obtaining good absorption is to completely dissolve the steroid in a pharmaceutical dosage form, but the steroid must have an optimal lipophilic/lipophobic ratio for optimal dermal absorption. At present, attempts to achieve this optimum lipophilic/lipophobic balance utilize the micronization of the water-insoluble steroid prior to or after incorporation into the oil-in-water or water-in-oil emulsified base or oleaginous base. However, the water content of such emulsion vehicles generally makes them less efficient in the release of the medicinal steroid to the patient's skin. Proper dispersion of the steroid in the oleaginous bases is also a problem that results in inefficient absorption.

In order to obviate the disadvantages of utilizing a water-containing composition, it has previously been found useful to formulate a steroid with a saturated fatty alcohol, a glycol solvent and a compatible plasticizer to give an anhydrous, water-deteriorable product (U.S. Pat. No. 3,952,930). However, this type of composition lacks the good occlusive covering ability afforded by an oleaginous base since it is in the form of a fluid and is also subject to water-deterioration, e.g., the sweat of the patient's skin.

A preferred ointment would incorporate the occlusive properties of an oleaginous base, but would obviate the greasy and removability aspects of such a base. A preferred product would therefore be water-removable, but water-insoluble. The present invention, most surprisingly, provides an ointment having the occlusive properties of an oleaginous base with an improved washability while reducing the greasiness typical of standard oleaginous base ointments and the water-solubility of the saturated fatty alcohol based ointments. Surprisingly, this invention utilizes an emulsion of a non-aqueous, water-miscible solvent-in-oil. This emulsion ointment functions as the prior art water-in-oil emulsions in that it provides the necessary lipophilic/lipophobic ratio needed for optimal dermal absorption of the steroid medicament, but lacks the detrimental water content of such emulsions. Since the emulsion of this invention incorporates an oleaginous base it retains the desirable occlusivity and water-insolubility of such conventional ointments. However, it is rendered less greasy (hence, more cosmetically elegant) and more water-washable through the use of the non-aqueous, water-miscible solvent as the phase-in-oil and the emulsifiers added to form the emulsion. Additionally, and most surprisingly, the dermal absorption of the steroid medicament is increased by the improved lipophilic/lipophobic ratio which the composition of my invention possesses.

This invention particularly relates to topical ointments which contain a steroid anti-inflammatory agent as the active ingredient and to methods of treating inflammatory conditions in patients by administering these ointments. The anti-inflammatory agents disclosed herein are of value in the topical treatment of dermatological disorders or like conditions responsive to anti-inflammatory drugs. Included within this category are disorders such as psoriasis, contact dermatitis (dermatitis venenata), atopic dermatitis (infantile eczema, allergic dermatitis), neurodermatitis (lichen simplex chronicus), lichen planus, eczema (including nummular eczema, hand eczema, eczematons dermatitis), intertrigo, dyshidrosis (pompholyx), seborrheic dermatitis, exfoliative dermatitis, solar dermatitis, stasis dermatitis and anogenital and senile pruritus.

Treatment with the ointments of this invention is usually accomplished by applying the ointment to completely cover the affected area. The usual frequency of application is twice daily, although adequate maintenance therapy for some patients may be achieved with less frequent application.

The ointment of the present invention comprises a therapeutically effective amount of an anti-inflammatory 17-mono or 17,21-diester of betamethasone in a non-aqueous base comprising 5–15% of a glycol solvent; 1–3% of propylene glycol monostearate as the principle emulsifying agent; 0–7% of white or yellow wax as the secondary emulsifying agent; and 70–90% of a petrolatum base.

The ointments of the present invention contain the steroid medicament in a therapeutically effective amount, e.g., an amount by weight of from 0.0005 to 5% of the total composition. Ranges of 0.005 to 0.5% are particularly suitable with a range of 0.01–0.2% by weight being most preferable.

The particular steroid medicaments for use in the composition of the present invention are the dermatologically acceptable 17-mono and 17,21-diesters of betamethasone disclosed in U.S. Pat. Nos. 3,312,590 and 3,529,060. Particularly preferred steroids are betamethasone 17,21-dipropionate and betamethasone 17-valerate. Another preferred steroid is betamethasone 17-benzoate.

The glycol solvent component is selected from the group consisting of 1,2-propylenediol, (propylene glycol), 2,3-butanediol, (2,3-butylene glycol), 2-methyl-2,4-pentanediol, (hexylene glycol), and mixtures thereof.

The glycol solvent must of course be pharmaceutically acceptable in the indicated concentration. The glycol solvent and steroid are selected so that the concentration of steroid in the glycol solvent is very close to the saturation point of the steroid in the chosen glycol solvent.

The primary emulsifying agent is propylene glycol monostearate, a compatible, pharmaceutically acceptable emulsifying agent. It is preferably present in an amount of about 1-2% by weight of the formulation. The secondary emulsifying agent, white or yellow wax, is present in an amount of 0-7% by weight. The secondary emulsifying agent may be omitted, but its use is desirable to obtain a formulation with a suitable melting point. A formulation containing about 6% by weight white wax is particularly suitable since this affords an ointment usable in the warmer climates. White wax (USP) is preferred over yellow wax (NF) since it affords a more appealing product. However, the white and yellow waxes are equivalent for the purposes of the invention.

The composition of the present invention may also contain up to 10% by weight of certain non-essential pharmaceutical adjuvants. These adjuvants may be added to improve consistency, homogeneity, spreadability, texture and appearance of the ointment.

The ointment of the present invention is manufactured in a conventional manner by thoroughly mixing the ingredients at ambient or elevated temperatures. Preferably, the steroid is first dissolved in the glycol solvent which is then mixed with the remaining ingredients.

If desired, additional mechanical agitation can be used as an intermediate or final step in the manufacturing process to impart more homogeneity or improve texture. Processing equipment suitable for these steps is known and includes heat exchangers, propeller mixers, colloid mills, homogenizers, roller mills and the like.

The ointments of the present invention have been found to be unexpectedly superior to previously known vehicles for use with topical steroids. For example, in preliminary tests, betamethasone dipropionate in the vehicle of this invention has been observed to have greater activity in comparison to its activity in the standard vehicle at the same concentration.

Additionally, and most advantageously, the ointments of the present invention have been found to be self-preserving when tested in standardized assays for the determination of growth of *Escherichia coli, Candida albicans, Staphylococcus aureus, Aspergillis niger,* and *Pseudomonas aeruginosa.* Thus, in most cases, no additional preservatives are necessary to the formulation.

The following examples describe in detail the compositions illustrative of the present invention. It will be apparent to those skilled in the art that many modifications, both of materials and methods, may be practiced without departing from the purpose and intent of this disclosure.

EXAMPLE 1

| Betamethasone Dipropionate Ointment (0.05%) | |
|---|---|
| Ingredients | mg/g |
| Betamethasone 17,21-dipropionate | 0.64 * |
| Propylene Glycol Monostearate | 20.00 |
| Propylene Glycol USP (1,2-propylenediol) | 100.00 |
| White Wax USP | 60.00 |

| -continued | |
|---|---|
| Betamethasone Dipropionate Ointment (0.05%) | |
| Ingredients | mg/g |
| White Petrolatum USP | 819.36 |

* equivalent to 0.5 mg betamethasone

Procedure

Heat the propylene glycol to about 50° C. Dissolve the betamethasone dipropionate in the propylene glycol using a moderate-speed agitator. Heat and melt the white petrolatum, white wax and propylene glycol monostearate together in a stainless steel bowl equipped with a moderate-speed mixer. Stir until the mixture is uniform and continue heating to 65°-70° C. Strain through 80-mesh screen into stainless steel bowl equipped with moderate-speed agitator and keep the temperature at about 60° C. Charge the propylene glycol solution into the oily mixture using moderate-speed agitation during the addition. Continue mixing for about 15 minutes while maintaining the temperature of about 55°-60° C. Mix while cooling to 30° C or until the ointment solidifies completely. Package in suitable tubes for dispensing.

EXAMPLE 2

| Betamethasone Valerate Ointment (1.05%) | | |
|---|---|---|
| Ingredients | | |
| Betamethasone 17-valerate | | 1.275 mg/g * |
| Propylene Glycol USP (1,2-propylenediol) | | 60.00 mg/g |
| Propylene Glycol Monostearate | | 10.00 mg/g |
| White Wax USP or Yellow Wax NF | | 60.00 mg/g |
| White Petroleum USP | q.s. | 1.00 g |

* equivalent to 1.05 mg betamethasone

Procedure

The procedure detailed in Example 1 is followed using the betamethasone 17-valerate in place of the betamethasone 17,21-dipropionate.

EXAMPLE 3

An ointment of the present invention as prepared in Example 1 was tested in a bilateral paired psoriasis study using a conventional betamethasone 17,21-dipropionate ointment consisting of 0.64 mg/g betamethasone 17,21-dipropionate, 50.0 mg/g mineral oil and 949.36 mg/g white petrolatum. Results of the bilateral paired comparison study [P values based on two-tailed sign test] indicate the ointment of Example 1 to be significantly ($p \leq 0.05$) more effective than the conventional ointment in the treatment of patients with chronic, stubborn psoriasis, based on the following results:

1. The proportion of results favoring the ointment as prepared in Example 1, based on comparison of severity of treated sides, was significantly ($p \leq 0.01$, two-tailed) greater than the proportion favoring the conventional ointment for: erythema, induration, scaling, total symptom score, patient's global opinion ($p \leq 0.02$), and physician's global opinion.

2. Mean severity of erythema, induration, scaling and total symptom score was significantly less ($p \leq 0.05$) for the ointment prepared as in Example 1.

3. Mean percent reduction in severity of erythema, induration, scaling and total symptom score was significantly less for the ointment prepared as in Example 1.

What is claimed is:

1. A method of treating inflammation which comprises applying to the skin a topical formulation comprising an amount effective to treat said inflammation of a dermatologically acceptable anti-inflammatory 17-mono or 17,21-diester of betamethasone in a non-aqueous, water-miscible solvent-in-oil base comprising
   5–15% of a non-aqueous, water-miscible solvent consisting essentially of a glycol solvent selected from the group consisting of
   1,2-propylenediol, butylene glycol, hexylene glycol and mixtures thereof;
   1–3% of propylene glycol monostearate;
   0–7% of white or yellow wax; and
   70–90% of petrolatum.

2. The method of claim 1 wherein the 17-mono or 17,21-diester of betamethasone is betamethasone 17,21-dipropionate.

3. The method of claim 1 wherein the 17-mono or 17,21-diester of betamethasone is betamethasone valerate.

4. The method of claim 1 wherein the 17-mono or 17,21-diester of betamethasone is present in an amount of 0.01–0.2% by weight.

5. The method of claim 1 wherein the glycol solvent is 1,2-propylenediol.

6. The method of claim 1 wherein the wax is white wax.

7. A topical ointment for the treatment of inflammation which comprises an amount effective to treat said inflammation of a dermatologically acceptable anti-inflammatory 17-mono or 17,21-diester of betamethasone in a non-aqueous, water-miscible solvent-in-oil base comprising
   5–15% of a non-aqueous, water-miscible solvent consisting essentially of a glycol solvent selected from the group consisting of 1,2-propylenediol, butylene glycol, hexylene glycol and mixtures thereof;
   1–3% of propylene glycol monostearate;
   0–7% of white or yellow wax; and
   70–90% of petrolatum.

8. The ointment of claim 7 wherein the 17-mono or 17,21-diester of betamethasone is betamethasone 17,21-dipropionate.

9. The ointment of claim 7 wherein the 17-mono or 17,21-diester of betamethasone is betamethasone 17-valerate.

10. The ointment of claim 7 wherein the 17-mono or 17,21-diester of betamethasone is present in an amount of 0.01–0.02% by weight.

11. The ointment of claim 7 wherein the glycol solvent is 1,2-propylenediol.

12. The ointment of claim 7 wherein the wax is white wax.

13. A method of treating psoriasis which comprises applying to the skin an ointment of claim 7.

14. A method of treating psoriasis which comprises applying to the skin an ointment of claim 8.

15. A method of treating psoriasis which comprises applying to the skin an ointment of claim 9.

16. A method of treating psoriasis which comprises applying to the skin an ointment of claim 10.

17. A method of treating psoriasis which comprises applying to the skin an ointment of claim 11.

18. A method of treating psoriasis which comprises applying to the skin an ointment of claim 12.

* * * * *

UNITED STATES PATENT AND TRADEMARK OFFICE
CERTIFICATE OF CORRECTION

PATENT NO. : 4,070,462
DATED : JANUARY 24, 1978
INVENTOR(S) : VARDA ECKER

It is certified that error appears in the above—identified patent and that said Letters Patent is hereby corrected as shown below:

In claim 10, line 3, change "0.02" to --0.2--

*Signed and Sealed this*

*Ninth* Day of *February 1982*

[SEAL]

Attest:

Attesting Officer

GERALD J. MOSSINGHOFF

*Commissioner of Patents and Trademarks*